United States Patent [19]

Bollenrath et al.

[11] Patent Number: 4,778,765

[45] Date of Patent: Oct. 18, 1988

[54] METHOD OF DETERMINING VISCOSITY NUMBER DURING THE OXIDATIVE COUPLING REACTION OF PHENOLS TO FORM POLYPHENYLENE ETHERS

[75] Inventors: Franz-Michael Bollenrath, Marl; Martin Bartmann, Recklinghausen, both of Fed. Rep. of Germany

[73] Assignee: Huls Aktiengesellschaft, Marl, Fed. Rep. of Germany

[21] Appl. No.: 41,338

[22] Filed: Apr. 22, 1987

[30] Foreign Application Priority Data

May 2, 1986 [DE] Fed. Rep. of Germany ....... 3614995

[51] Int. Cl.$^4$ ...................... G01N 33/22; G01N 35/08
[52] U.S. Cl. ..................................... 436/128; 528/212; 436/52
[58] Field of Search .................... 436/2, 128; 528/212; 524/876, 736; 523/303; 73/534

[56] References Cited

U.S. PATENT DOCUMENTS 3,478,111 11/1969 Bruce ................................. 436/128
4,607,085 8/1986 Penczek et al. ..................... 528/212

OTHER PUBLICATIONS

*Encyclopedia of Chemical Technology*, pp. 290–299.

Primary Examiner—Barry S. Richman
Assistant Examiner—Lyle Alfandary Alexander
Attorney, Agent, or Firm—Oblon, Fisher, Spivak, McClelland & Maier

[57] ABSTRACT

A method of continuous rapid determination of the J-value during the oxidative coupling reaction of phenols to form polyphenylene ethers. Solution of a defined temperature is withdrawn from the reaction mixture, the viscosity of the solution is measured in a Couette viscometer, and the J-value is determined using a calibration curve or mathematical means.

2 Claims, 2 Drawing Sheets

METHOD OF DETERMINING VISCOSITY NUMBER DURING THE OXIDATIVE COUPLING REACTION OF PHENOLS TO FORM POLYPHENYLENE ETHERS

BACKGROUND OF THE INVENTION

1. Field of the Invention:

The invention relates to a simple method of determining the J-value of polyphenylene ethers (PPEs) during the oxidative coupling reaction. The J-value is a measure of the molecular weight of the polymer (see DIN 53 728).

2. Discussion of the Background:

It is well known that the viscosity number does not vary markedly during the early part of the oxidative coupling reaction to form polyphenylene ethers. Only in the last third of the reaction progress does the J-value rise particularly rapidly, namely exponentially. In practice, one is interested in producing a PPE with a molecular weight which is as uniform as possible. Also, one desires a PPE with a given J-value, since PPEs with lower or higher J-values have disadvantages in a given application.

This requires an ability to accurately and rapidly determine the J-value during the oxidative coupling reaction, in order to be able to stop the reaction at the desired termination point. This has been a continuing problem in the production of PPEs.

If one attempts the determination by measuring the amounts of oxygen fed and withdrawn, a measurement which itself is difficult, the result is a very inadequate indication of the course of the reaction. One may not use spectroscopic techniques to follow the reaction either, because the reaction solutions contain catalysts and strongly colored impurities. Further, termination at the desired point requires a measurement of the PPE polycondensation which is capable of being performed in less than one minute.

In general, the use of a viscometer to measure the J-values of polymer solutions is known. DIN 53 728 provides that the solvent be evaporated off, a specified dilute solution be prepared, and the viscosity then be determined in an Ubbelohde viscometer according to DIN 51 562. Such a method is very time-consuming, and therefore unsuitable in the present case. It is also known to follow chemical processes in situ using a viscometer in a flow-through mode. However, this poses the following problems when attempted in connection with the oxidative coupling reaction of phenols:

(1) At the beginning of the reaction the viscosity of the reaction solution is extremely low, being only 1-6 mPa sec, and is not even determinable by an ordinary measuring apparatus;

(2) Many viscometers require specially prepared samples; and (3) PPEs always deposit to some degree on the walls of the measuring instrument, with major effects on the measurements. Accordingly, normal capillar viscometers are fundamentally unsuitable.

European Pat. No. 0 144 106 discloses a method for determining the viscosity of PPEs during the oxidative coupling reaction. This method consists of intermittently taking samples from the reactor, and terminating the polymerization by adding a liquid. As soon as one has obtained a clear, homogeneous solution, one can measure the transit time of the solution through a capillary tube viscometer, whereby the viscosity, and thereby the molecular weight, is determined by comparison with standard values. This method must be carried out discontinuously, which is a disadvantage. When the viscosity is rising rapidly during the critical end stage of the oxidative coupling reaction, one cannot obtain the instantaneous viscosity number of the reaction solution by this method.

A need continues to exist therefore for a rapid continuous method of determining the J-value during the oxidative coupling reaction of phenols to form polyphenylene ethers.

SUMMARY OF THE INVENTION

Accordingly, one object of the present invention is to provide a method for the continuous rapid determination of the J-value during the oxidative coupling reaction of phenols to form polyphenylene ethers.

Another object of the invention is to provide a method of determining the J-value which provides accurate values in the critical region where the J-value are increasing rapidly.

A further object of the invention is to provide a method for the determination of the J-value in which the deposition of PPE in the measuring instrument is low.

These objects and other objects of the present invention which will become apparent from the following specification have been achieved by the present method for the determination of the J-value during the oxidative coupling reaction of phenols to form polyphenylene ethers, comprising the steps of:

withdrawing reaction solution from the reaction mixture at a reaction temperature between 0° and 60° C., preferably 20' and 40° C.;

measuring the viscosity of said solution in a Couette viscometer; and determining the J-value using a calibration curve or mathematical means.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

In FIG. 1 the terms $F_c$, $CO_2R$, TCR and M refer to the following definitions FC - flow control
$CO_2R$ - registration of oxygen concentration
TCR - temperature control and registration
M - motor In FIG. 2, the term SKT means scale marks on the viscometer scale.

DETAILED DESCRIPTION OF THE PREFERRED EMBODIMENTS

Figure 1:
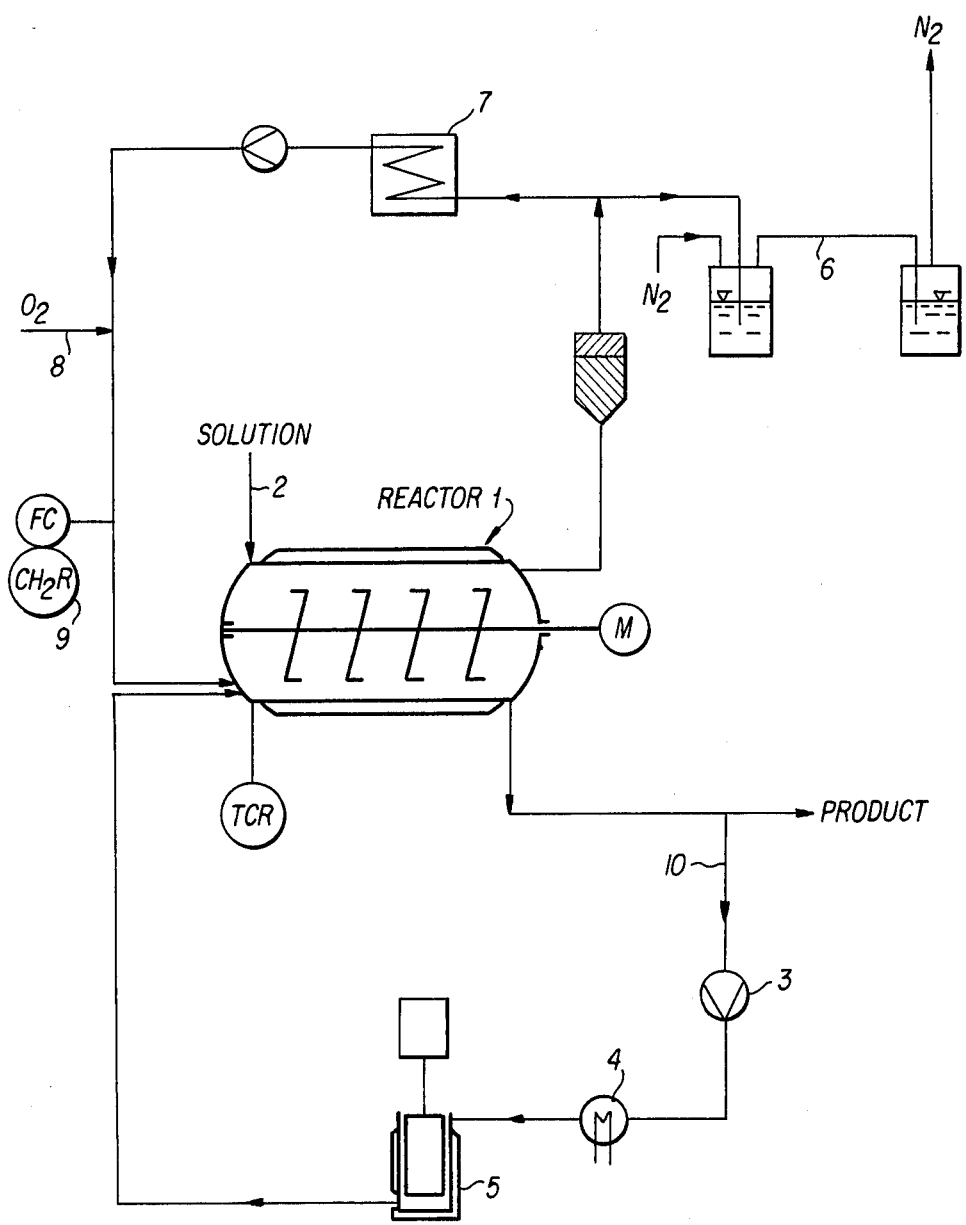
FIG. 1 illustrates a preferred embodiment of an apparatus for the continuous rapid determination of viscosity numbers.

A method has been discovered, in connection with the invention, which avoids the drawbacks of prior art processes. This method consists of taking a solution from the PPE reactor and passing it at a defined temperature through a Couette viscometer, preferably thermostatically controlled, measuring the viscosity, and determining the J-value from a calibration curve or by other means. The solution can then be returned to the reactor. If necessary, the viscometer can be rinsed with the solvent after each production run.

Although the inventive method does not correspond exactly to DIN 53 728, it has proved surprisingly practicable.

At the beginning of the polycondensation, of course, the inventive method returns only rough values. However in the critical region of higher J-14 values in the range of about 14–30 mPa sec, the method is very accurate. It has been discovered that there is a relationship between the time up to the desired viscosity and the achievable J-value.

The inventive method is generally confined to the given solvent and the given concentration of the polymer in the solvent. However, by the use of mathematical relations, or empirically by constructing calibration curves, it is possible to extend operations to concentrations and solvents different from the standard ones.

In particular, the inventive method enables the viscosity to be measured in the actual solutions, with the viscosity number determined from the viscosity. The time to achieve the measurement is about 10 sec, depending on the mean flow speed and the length of the flow path in the rheometer. Preferably, the flow path should be kept short.

The oxidative coupling reaction of di-ortho-substituted and certain sterically hindered mono-ortho-substituted phenols to form PPEs is described in detail in German OS Nos. 32 24 692, 32 24 691, and 33 13 864, and in reference cited therein.

Reaction solution is withdrawn from the reactor at the start of the reaction. Preferably, the withdrawal is continuous. During the early stages of polymerization it is preferable to withdraw samples intermittently at short intervals; however, in the final stages the viscosity number increases so rapidly that the reaction cannot be terminated properly unless the reaction solution is withdrawn continuously for testing and the viscosity changes are followed closely. Viscosities must be measured at a known temperature. Preferably the temperature will be constant and in the range of the reaction temperature. Preferred temperatures are temperatures which are normally used in polyphenylene ether polymerizations and are well known to those skilled in the art. See for example, U.S. Pat. Nos. 3,306,874 and 3,306,875.

Accordingly, it is preferable to thermostatically control the temperature of the solution withdrawn from the reactor, by means of a heat exchanger, and then to pass the solution through the Couette viscometer which is maintained at this same temperature. The structure of a Couette viscometer is given, for example, in "Ullmanns Encyklopaedie der Technischen Chemie", Vol. 5, pp. 765 ff (1980).

The reaction solution which has been withdrawn can then be returned to the reactor. Preferably, the measurement of viscosity is carried out in a viscometer through which the liquid flows in a "bypass" fashion. The flow relocity is set in known fashion, the criterion being that the viscosity measurement not be greatly influenced by the axial flow through the rheometer. The J-values can be determined from the viscosity values via the above-mentioned calibration curve. In principle it is possible to determine the J-values in other ways, e.g. using a mathematical approximation formula. See Vollmert, Grundriss der makromolekularen Chemie, Springer Verlag, 1962.

Other features of the invention will become apparent in the course of the following description of an exemplary embodiment which is given for illustration of the invention and is not intended to be limiting thereof.

EXAMPLE

A thermally stabilized reactor 1 (SEE FIG. 1) filled to about 90% with reaction solution is fed continuously with oxygen (see German OS No. 33 13 864, Example 2). In order to control the $O_2$ content of the gas at the reactor input, a partial stream is withdrawn from the reactor and passed through a loop 7 to a measuring apparatus 9. The submerged pipe 6 controls the pressure. The progress of the polycondensation is measured with the aid of the loop 10 comprising a pump 3, a heat exchanger 4, and a Couette rheometer 5 which continuously measures the viscosity of the solution.

Figure 2:
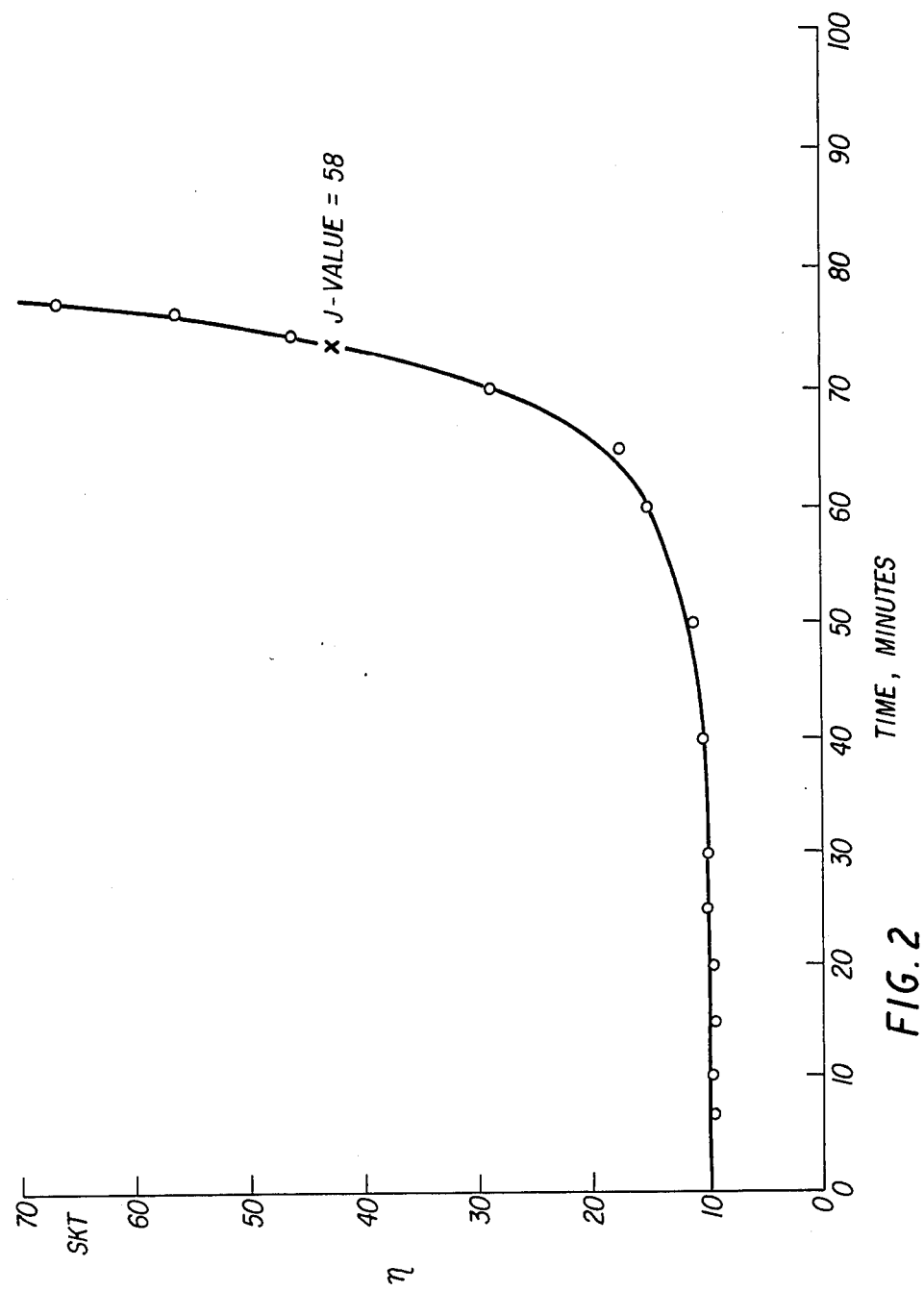
FIG. 2 is a plot of viscosity versus time for a sample oxidative coupling reaction to produce polyphenylene ether.

A plot of viscosity versus time is shown in FIG. 2.

The desired end-point viscosity number is 58, corresponding to 42 scale units on the indicator of the rheometer. After 74 min this value is reached, and the reaction is terminated by adding an excess of 50% acetic acid.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for the determination of the J-value during the oxidative coupling reaction in a solvent of a phenol to form a polyphenylene ether, comprising the steps of:
    continuously withdrawing reaction solution from the reaction mixture during the reaction at a temperature between 0° and 60° C. using a recycle loop in a bypass fashion;
    measuring the viscosity of said solution in a Couette viscometer; and
    determining the J-value using a calibration curve or mathematical approximation means.

2. The method of claim 1, wherein said temperature is thermostatically controlled.

* * * * *